United States Patent [19]

Lenfers et al.

[11] Patent Number: 5,360,266
[45] Date of Patent: Nov. 1, 1994

[54] CONTROL AND ANALYSIS CIRCUIT DEVICE FOR MEASURING REACTION HEAT

[75] Inventors: Martin Lenfers, Vaihingen/Enz; Johann Riegel, Moeglingen, both of Germany

[73] Assignee: Robert Bosch GmbH, Stuttgart, Germany

[21] Appl. No.: 79,617

[22] Filed: Jun. 18, 1993

[30] Foreign Application Priority Data

Jul. 3, 1992 [DE] Germany ............... 4221922

[51] Int. Cl.$^5$ ............... G01N 25/22; G01N 27/12
[52] U.S. Cl. ............... 374/36; 374/164; 73/23.31; 73/25.01; 422/94
[58] Field of Search ............... 374/36, 164, 11; 422/94; 73/23.31, 25.01

[56] References Cited

U.S. PATENT DOCUMENTS

| | | | |
|---|---|---|---|
| 2,805,134 | 9/1957 | Strange | 73/25.01 |
| 4,029,472 | 6/1977 | Micheli et al. | 374/36 |
| 4,063,898 | 12/1977 | Fisher | 374/36 |
| 4,533,520 | 8/1985 | Bossart et al. | |
| 4,541,988 | 9/1985 | Tozier et al. | |
| 4,779,078 | 10/1988 | Ciolli | 73/23.31 |
| 4,817,414 | 4/1989 | Hagen et al. | 73/23.31 |
| 4,870,025 | 9/1989 | Hurley et al. | |
| 5,055,269 | 10/1991 | Palumbo et al. | 73/23.31 |

FOREIGN PATENT DOCUMENTS

| | | | |
|---|---|---|---|
| 0314919 | 5/1989 | European Pat. Off. | |
| 2670291 | 6/1992 | France . | |
| 1256320 | 12/1967 | Germany | 73/25.01 |
| 271379 | 8/1989 | Germany . | |
| 3844023 | 6/1990 | Germany . | |
| 0291638 | 7/1991 | Germany | 374/36 |
| 4020385 | 1/1992 | Germany . | |
| 4025875 | 2/1992 | Germany . | |
| 0038645 | 2/1985 | Japan | 374/36 |
| 2091882 | 8/1982 | United Kingdom . | |
| 2167192 | 5/1986 | United Kingdom | 374/36 |
| 0618657 | 8/1978 | U.S.S.R. | 374/36 |
| 2143645 | 2/1985 | U.S.S.R. | 374/36 |
| 9105998 | 5/1991 | World Int. Prop. O. | 374/36 |

Primary Examiner—Diego F. F. Gutierrez
Attorney, Agent, or Firm—Michael J. Striker

[57] ABSTRACT

The reaction heat sensor and control and analysis devices for measuring the concentration of reactive species in a medium includes a temperature dependent measuring resistor and a reference resistor connected in series. Both resistors, which are supplied with a constant alternating current by a constant current generator, are heated with a heating resistor. By analysis of the voltage drop at the reference resistor the heating resistor is regulated so that the temperature of the reference resistor and thus its reference resistance is kept constant. Thus it is guaranteed by control circuitry that the temperature of the measuring resistance is kept constant when no heat is generated by reaction on exposure to the medium. If a reaction occurs at the measuring resistor, the temperature of the measuring resistance changes and with it the voltage drop across the measuring resistor, which is analyzed and is a direct measure of the heat produced by the reaction.

11 Claims, 4 Drawing Sheets

CONTROL AND ANALYSIS CIRCUIT DEVICE FOR MEASURING REACTION HEAT

BACKGROUND OF THE INVENTION

The present invention relates to a reaction heat sensor including a control and analysis circuit device for measuring reaction heat.

A control and analysis circuit device for measuring reaction heat is known, comprising at least two temperature dependent resistors through which current flows and which form a voltage divider and an analyzer circuit means connected to the voltage divider. One of the resistors is coated with a catalytically active layer and a catalytically inactive resistor is provided as a reference resistor. Both resistors are exposed to a medium containing reactive components which react with the resistor coated with the catalytically active layer to generate a heat of reaction to be measured.

For gas analysis, especially for determination of a content of a combustible gas, a reaction heat sensor can be used in oxygen-containing gases. The reaction heat sensor contains, as mentioned above, two temperature-dependent resistors through which current flows and which are connected in series with each other. A first resistor is provided with a catalytically active surface and a second reference resistor is provided without a catalytically active surface. The resistor provided with the catalytically active surface acts as a measuring resistor.

In case reactive components are present in the measured gas containing an oxygen excess, e.g. CO or other oxidizable gases or reducible gases, such as NOX, a reaction heat is produced by reaction on the catalytically active surface of the measuring resistor, which increases the temperature of the measuring resistor. Thus the value of the resistance of the measuring resistor changes. This change is analyzed with a following analysis device and used for determination of the content of oxidizable gases.

Reaction heat sensors are used, for example in order to determine the composition of exhaust gases, such as carbon monoxide, nitrogen oxide and unburned or partially burned hydrocarbons, in an internal combustion engine, so that the internal combustion engine can be operated so that the emission of hazardous pollutants is kept as small as possible.

This type of reaction heat sensor, is described in DE-OS 40 20 385. One embodiment of this known sensor has two temperature sensing elements, which are both heated by a heating resistor. One of the temperature sensing elements experiences an additional heating because of the exothermic reaction occurring on its surface, while the other temperature sensing element is arranged and/or protected so that no exothermic reaction results.

This known heat content sensor has the disadvantage however that no temperature control is performed, which guarantees that the temperature of the reference temperature sensing element remains constant. When the temperature of the gas being analyzed changes during measurement, inaccuracies can occur.

Another sensor for determining the gas concentration in a gas mixture by measuring reaction heat during oxidation of combustible gas is described in DE-OS 38 44 023. In this sensor thin film resistances, which act as measuring and heating resistors, are used. They are covered with a protective layer so that they do not come into contact with an oxidizable gas.

A catalytically active layer, on which oxidation occurs and additional heating occurs, is applied to the region heatable by the thin wire resistor. The gas concentration to be measured is determined from this additional heating.

SUMMARY OF THE INVENTION

It is an object of the present invention to provide an improved reaction heat sensor including a control and analysis circuit device, which does not have the above-described disadvantages.

According to the invention the reaction heat sensor and control and analysis means comprises a voltage divider including a reference resistor having a reference resistance and a measuring resistor coated with a catalytically active layer to promote reaction between reactive species in a medium; means for exposing the measuring resistor to the medium so that the reactive species in the medium react at the measuring resistor and generate a heat of reaction to be measured; means for making the reference resistor inactive to the medium; controlling means for keeping the resistor, means for measuring a voltage drop across the reference resistor and means for using the voltage drop measured by the means for measuring to keep reference resistance of the reference resistor constant, the controlling means including heating means for heating the reference resistor and the measuring the reference resistance of the reference resistor constant and means for analyzing a change in a resistance value of the measuring resistor to determine the reaction heat when the measuring resistor is exposed to the medium.

In a preferred embodiment the means for making the reference resistor inactive to the medium comprises a catalytically inactive layer applied to the reference resistor to render the reference resistor nonreactive to the medium. In another embodiment the means for making the reference resistor inactive to the medium comprises an impermeable housing enclosing the reference resistor so as to separate the medium from the reference resistor.

In a preferred embodiment the control and analysis circuit device further comprises means for maintaining a current flowing through the measuring resistor constant, which can be an alternating current generator. Voltage limiting means are advantageously connected to the alternating current generator.

The heating means can comprise a heating resistor and means for controlling a heating current flowing through that heating resistor. The heating resistor is advantageously connected between a source of voltage and ground, the heating resistor being connected to ground via a switching means, which is advantageously a transistor controlled according to a voltage drop across the reference resistor.

The control and analysis circuit device and reaction heat sensor according to the invention has the advantage that a stable measurement of the content of the oxidizable gases of the medium to be tested is possible, since a separate temperature measurement is not required. Because of that, it is guaranteed that no inaccuracies occur during the measurement time due to shifts in temperature. This is guaranteed, because both the measuring and also the reference resistor associated with it are heated with the help of a controlling heating means. This heating is regulated so that the value of temperature of the reference resistor and thus its reference resistance remains constant. Thus the change in the resistance value of the measuring resistor depends only on the heat of reaction at the measuring resistor and can thus particularly advantageously be used for determination of a content of the oxidizable gases.

Further it is advantageous that voltages are measured by the control and analysis circuit device associated with the heat content sensor, which guarantees a reliable and accurate measurement—i.e. the control and analysis circuit device contains means for measuring voltages.

In a preferred embodiment both resistors are NTC- or PTC-resistors, so that particularly economical sensor results.

The uniform heating of the measuring and reference resistors allows in a particularly advantageous manner a measurement, which is independent of the temperature of the gas and independent of the current.

BRIEF DESCRIPTION OF THE DRAWING

The objects, features and advantages of the present invention will now be illustrated in more detail by the following detailed description, reference being made to the accompanying drawing in which.

DESCRIPTION OF THE PREFERRED EMBODIMENTS

Figure 1:
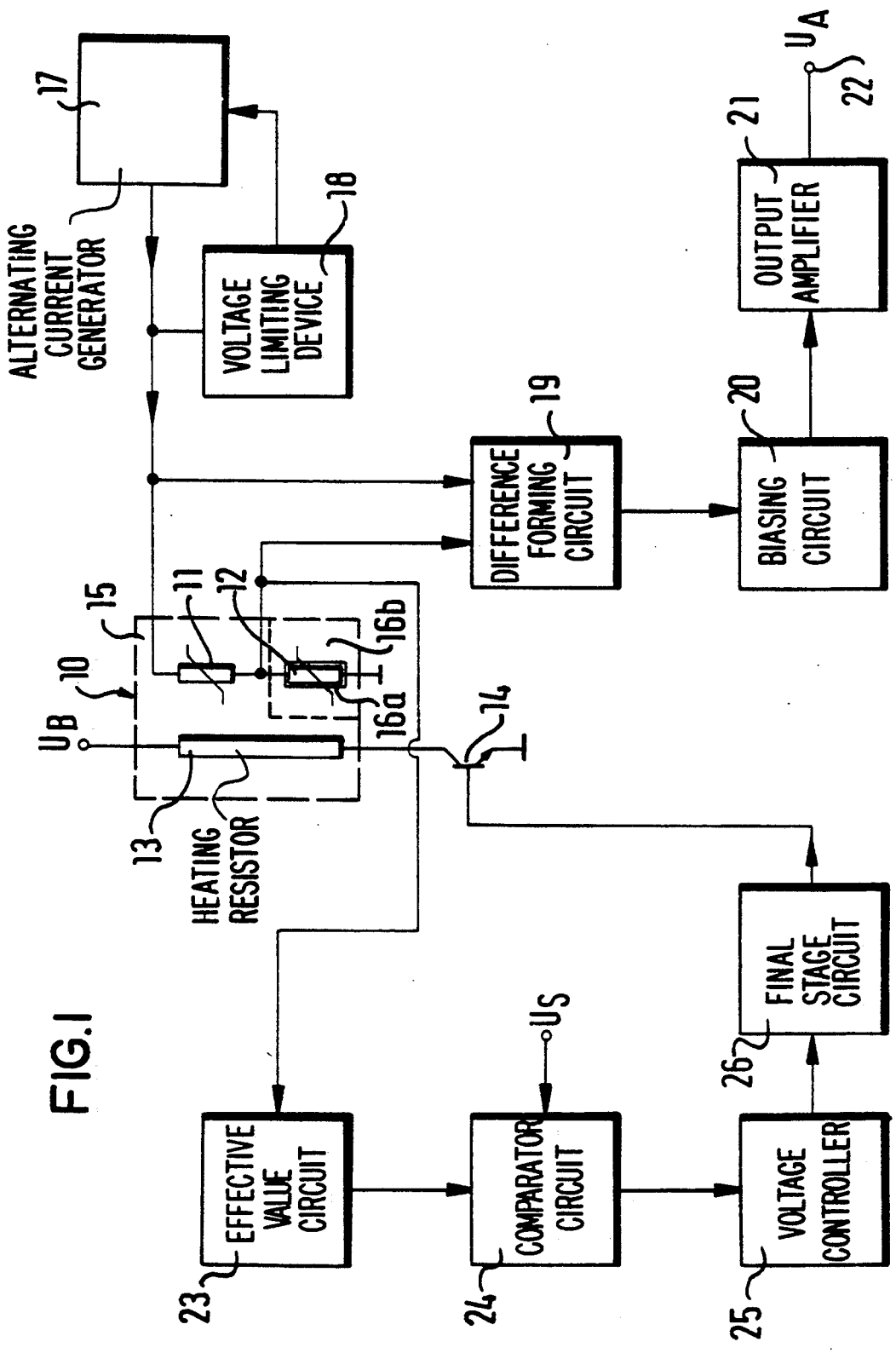
FIG. 1 is a block diagram of a sensor and associated control and analysis circuit device according to the invention.

The heat content sensor 10 shown in FIG. 1 comprises a measuring resistor 11 and a reference resistor 12 connected in series with it. A heating means 13 is associated with both of the resistors 11,12. The heating means 13, advantageously a heating resistor, is connected to a source of battery voltage $U_B$ on one end and on the other end by a transistor 14 to ground. The resistors 11 and 12 are NTC-resistors, also other temperature dependent resistors, e.g. PTC-resistors are usable, in the control and analysis circuit device shown in the drawing.

The sensor 10 is surrounded by a housing 15, which is formed so that the gas to be analyzed can surround the measuring resistor 11 and the reference resistor 12. The measuring resistor 11 has a catalytically active surface for catalyzing reactions producing heat, e.g. the reaction of oxygen and CO. In one preferred embodiment the reference resistor 12 is passive, e.g. a catalytically inactive layer 16a can be applied to the surface of this resistor to make the surface passive.

In another embodiment the housing 15 is only gas permeable in the vicinity of the measuring resistor 11, while it is not permeable in the vicinity of the reference resistor 12. Thus the nongaspermeable portion of the housing is indicated with 16b.

An output of an alternating current generator 17 is electrically connected with an end of the measuring resistor 11 not connected to the reference resistor 12 and with an input of a voltage limiting device 18, which has an output connected with an input of the alternating current generator 17.

Both the input of the voltage limiting device 18 and the output of the alternating current generator 17 are connected electrically to an input of a difference forming circuit 19, whose second input is connected with a connection point between the measuring resistor 11 and the reference resistor 12.

The difference forming circuit 19 is connected to biasing circuit 20 and a following output amplifier 21 having a terminal 22, to which the output signal $U_A$, which represents the desired characteristic variable, is sent.

The end of the measuring resistor 11 directly connected to the reference resistor 12 or the connection point between them is connected electrically to an effective value circuit 23, so that the voltage between the measuring resistor 11 and the reference resistor 12 is transformed to an effective value. This effective value is then fed to a comparator circuit 24, which is also fed a set value $U_S$ which is compared to the effective value.

The comparator circuit 24 is connected further to a voltage controller 25, which acts on a base of the transistor 14 via a final stage circuit 26.

Figure 2:
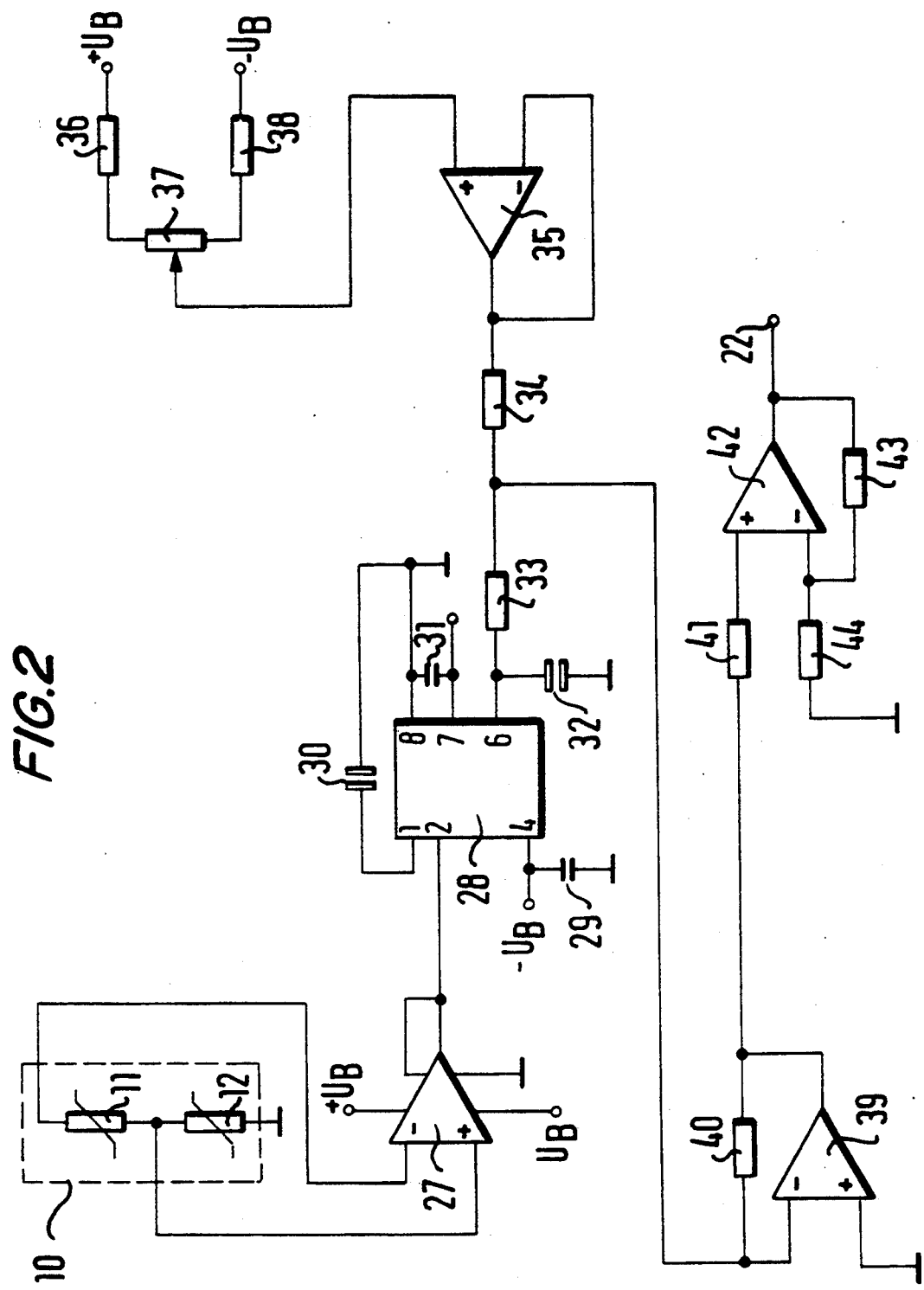
FIGS. 2 to 4 are circuit diagrams for portions of the associated control and analysis circuit of the invention.

A preferred embodiment of a portion of the control and analysis circuit means according to the invention is shown in FIG. 2. The voltage divider circuit having the measuring resistance 11 and the reference resistance 12 of the sensor 10 is connected with both inputs of a differential amplifier 27, an end of the measuring resistor 11 not connected to the reference resistor 12 being connected electrically with the inverting input of the differential amplifier 27 and the other end of the measuring resistor connected with the reference resistor 12 being connected with the noninverting input of the differential amplifier 27. The differential amplifier 27 is driven between a positive voltage $+U_B$ and a negative voltage $-U_B$ and its output is connected with an integrating circuit 28. The effective value circuit 23 includes the differential amplifier 27 and the integrated circuit 28.

This effective value circuit includes four condensers 29, 30, 31, 32, which are connected between the individual inputs and outputs of the integrating circuit (IC) and ground. Also the IC 28 is still connected to positive and negative battery voltage $+U_B$, $-U_B$.

The output of the integrating circuit (IC) 28 is connected electrically by a resistor 33 to the inverting input of the operational amplifier 39, which together with the resistors 33, 34 and 40 form an inverting adder means.

The inverting input of the operational amplifier 39 is connected with the output by the resistor 40, while the noninverting input is connected to ground. This part of the circuit acts as an adder biasing device.

The output of the operational amplifier 35 producing the biasing voltage, whose noninverting input is connected with a voltage divider 36,37,38 between the positive and negative battery voltages, the variable resistor 37 being a voltage divider, is connected with the inverting input of the operational amplifier 39 by the resistor 34. The inverting input of the operational amplifier 35 is connected with its output and forms a voltage follower circuit.

The output of the operational amplifier 39 is connected by a resistor 41 with the noninverting input of an operational amplifier 42, whose output is the signal output 22.

An additional resistor 43 is connected across the output of the operational amplifier 42 and the inverting input. Also the inverting input is connected by a resistor 44 with ground. The operational amplifier 42 together with its components comprises the final amplifier circuit and/or the output amplifier.

Figure 3:
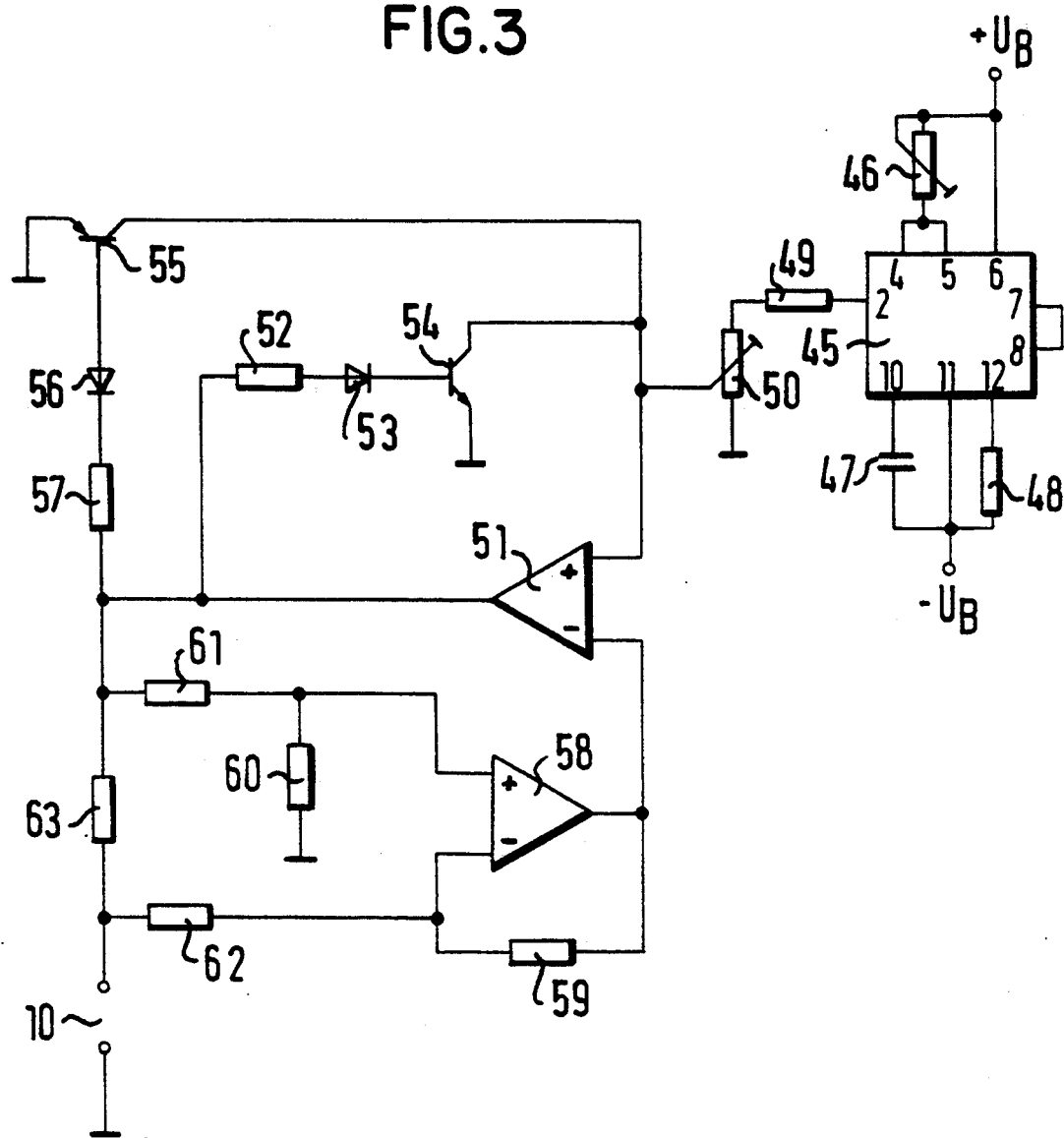

A preferred embodiment of the alternating current generator 17 and the voltage limiting circuit 18 is shown in FIG. 3. The alternating current generator 17 includes an integrating circuit (IC) 45, which is driven between positive and negative battery voltage $+U_B$, $-U_B$ and is connected to a variable resistor 46, a condenser 47 and a resistor 48.

The output of the integrating circuit 45 is connected by a voltage divider including a resistor 49 and a variable resistor 50, e.g. the slider of a potentiometer, with a circuit component of the voltage limiting circuit 18. The variable resistor 50 is connected on one end with the noninverting input of an operational amplifier 51, whose output is connected with the slider of a potentiometer 50 via a resistor 52, a diode 53 and a transistor 54. Furthermore the cathode of the diode 53 is connected to the base of the transistor 54, while its emitter is connected to ground and its collected to the slider of the resistor 50. The circuit elements 54, 53 and 52 serve for voltage limitation of the positive half wave, which is produced by the sine generator.

The voltage limitation of the negative half wave is performed with the help of the transistor 55, the diode 56 and the resistor 57, the collector of the transistor 55 is also connected with the resistor 50, while its emitter is connected to ground. The base of the transistor 55 is connected by the diode 56 and the resistor 57 with the output of the operational amplifier 51.

For constant current regulation the output of an additional operational amplifier 58 is connected with the inverting input of the operational amplifier 51. The output of the operational amplifier 58 is also connected with its own inverting input via resistor 59, while the noninverting input of operational amplifier 58 is connected via a resistor 60 with ground and via an additional resistor 61 with the output of the operational amplifier 51 and with the resistors 52 and 57.

The sensor 10 is connected by a current measuring resistor 63 with the output of the operational amplifier 51 and with the resistors 61, 57 and 52, and by the resistor 62 with the inverting input of the operational amplifier 58.

Figure 4:
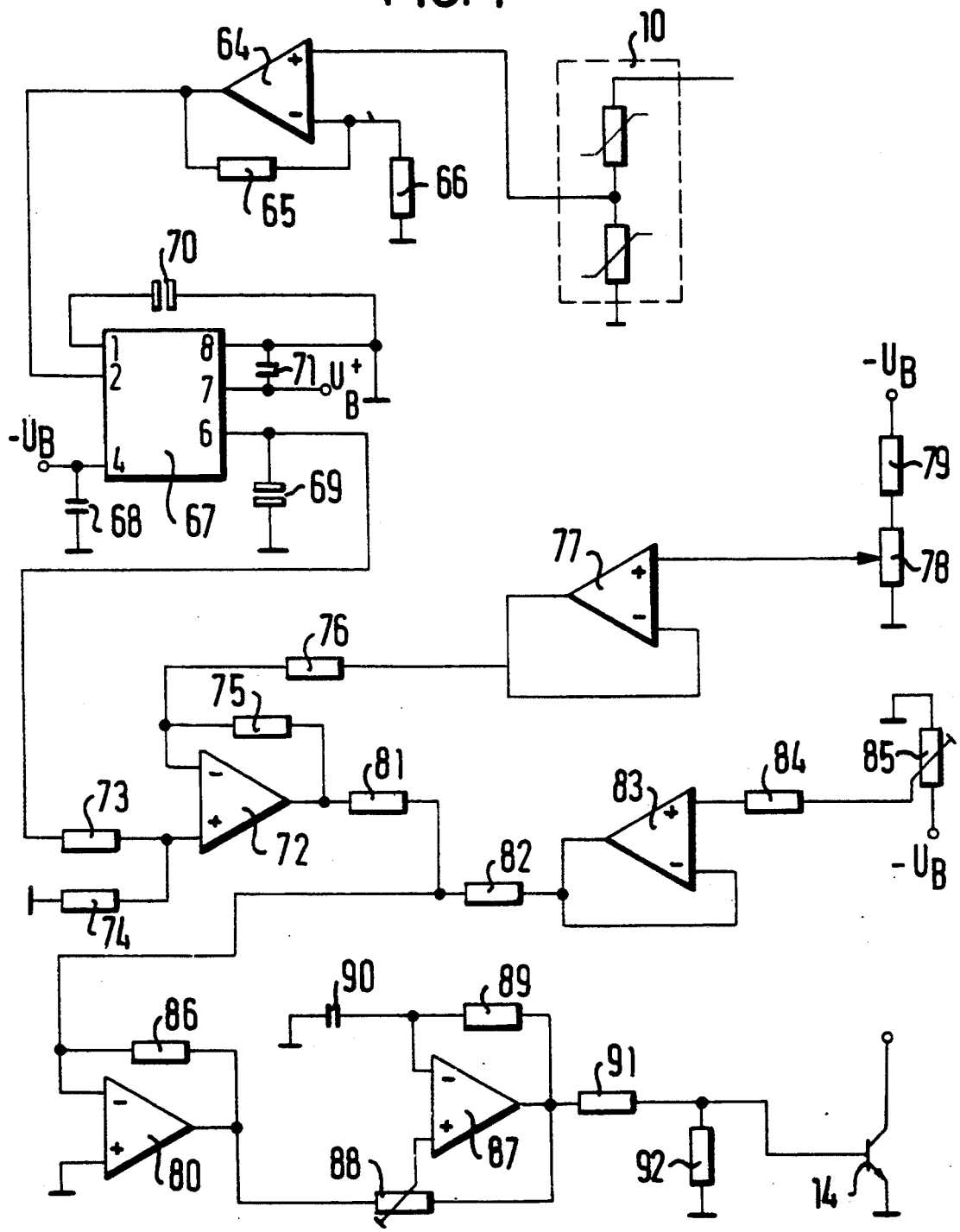

A preferred embodiment of the heating controller circuit for maintaining the temperature of the reference resistor constant is shown in FIG. 4. This circuit arrangement has a first operational amplifier 64, which is connected with a connection point between the measuring and reference resistors 11,12 of the sensor 10. A resistor 65 is connected between the output of the operational amplifier 64 and the inverting input. This inverting input is connected by a resistor 66 to ground. The operational amplifier 64 and associated circuit components act to amplify and decouple from the following circuitry.

The output of the operational amplifier 64 is connected to a circuit part, which forms effective voltage values and corresponds to the circuit represented by block 23 of FIG. 1. This circuit part comprises an integrated circuit 67, which is connected to ground and sources of the voltages $-U_B$, $+U_B$. It also has condensers 68, 69, 70 and 71, which either are connected between inputs of the integrated circuit or between an input of the integrated circuit and ground.

The comparator circuit 24, which is connected with the integrated circuit 67, has an operational amplifier 72, whose noninverting input is connected by a resistor 73 with the integrated circuit 67 and by another resistor 74 to ground. A feedback coupling resistor 75 is connected across the inverting input and the output of the operational amplifier 72. The inverting input of the operational amplifier 72 is also connected with an operational amplifier 77 via a resistor 76. The noninverting input of the operational amplifier 77 is connected with a potentiometer 78, which is part of a voltage divider, which also includes a resistor 79 which is connected between ground and and $-U_B$.

The operational amplifier 77 and the voltage divider 78,79 feed the set value to the comparator circuit.

The voltage control generator 25 contains a first operational amplifier 80, whose inverting input is connected by a resistor 81 with the comparator stage and is connected with an output of the operational amplifier 83 via a resistor 82.

The operational amplifier 83, whose noninverting input is connected by a resistor 84 with a voltage divider 85, which is connected across a source of voltage $-U_B$ and ground, forms a biasing means for the voltage controller 25. This has an additional operational amplifier 87 besides the already mentioned operational amplifier 80 with a feedback coupling resistor 86. The noninverting input of the operational amplifier 80 is connected to a voltage divider 88, which is connected between the output of the operational amplifier 80 and the output of the operational amplifier 87. A resistor 89 is connected between the inverting input of the operational amplifier 87 and its output. The inverting input of the operational amplifier 87 is connected by a condenser 90 to ground.

The output of the operational amplifier 87, at which a pulse with a variable input/output ratio arises, is connected by a resistor 91 with the base of a transistor 14, which again is connected with ground by the resistor 92.

The transistor 14 which is connected by its base to a final stage circuit 26 is the final component leading to the heating means, e.g a heating resistor, 13. The collector of transistor 14 is connected electrically to the heating means 13 and the emitter is connected to ground.

The operation of the above-described device is as follows:

The heat content sensor 10 is set so that the measuring resistor 11 with a catalytically active surface, preferably an NTC-resistor, is exposed to the medium to be measured, for example to the exhaust gas of a motor vehicle. The reference resistor 12 with the passive surface is arranged in the vicinity of the measuring resistor 11, however so that no heat flow is possible between the resistors. Both resistors contact the exhaust gas, and with convection present this gas acts on both resistors and causes no measurement errors.

Heating means 13 is located close to both resistors 11 and 12 so that both these resistors are at the same temperature when no gas reaction occurs. If however a gas reaction occurs at the measuring resistor, the temperature of the measuring resistor is increased so that the resistor and thus the voltage ratio changes at the voltage divider 11,12. These changes are used to determine the oxidizable gas composition.

It is possible to measure the voltage drop experienced by a constant current produced by the alternating current generator 17 both at the measuring resistor 11 and also at the reference resistor 12 by the voltage divider or potentiometer 11,12 and thus to obtain an output signal dependent on the concentration of the oxidizable gas from the measured voltage change. The current from the generator 17 is limited to a value which causes no overheating or too strong a load on the sensor by the voltage limiting device 18.

If the temperature of the reference resistance is kept constant by control of the heating by the heating means 13, the resistance change in the measuring resistor 11 depends only on the reaction heat.

The control of the temperature is performed at the reference resistor, since the voltage drop occurring at the reference resistor 12 is applied to comparator circuit 24 after an effective value formation. A predetermined voltage is used as the set value in the comparison, which is formed in the set value stage with operational amplifier 77 and the voltage divider 78 and 79 in FIG. 4.

The output voltage of the comparison or output of the comparator circuit 24 is applied to the voltage controller 25 which produces a voltage at its output with a variable input/output ratio. The voltage produced by the voltage controller 25 depends on this input/output ratio.

When the temperature at the reference resistor 12 drops, the input/output ratio changes so that the switched on phase is lengthened so that the transistor 14 remains conductive longer and thus the heating power applied by the heating means 13 is increased so that the temperature in the reference resistor 12 again increases. Should the conditions reverse and the temperature at the reference resistor increases, a reliable temperature control is guaranteed for the reference resistor 12 and also for the measuring resistor 11.

The circuit means in the blocks 19, 20 and 21 perform the analysis of the resistance change caused by the gas reaction and thus the temperature increase occurring at the measuring resistor. The voltage drop occurring at the measuring resistor 11 is determined thus in the difference forming circuit 19. After effective value formation and rectification as well as a suitable biasing a voltage is obtained dependent on the heat of reaction, which is available after final amplification at the output 22 and is a direct measure of the reaction heat and thus the composition of the oxidizable gas.

While the invention has been illustrated and reaction heat sensor and control and analysis circuit device for measuring a reaction heat, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims.

We claim:

1. Reaction heat sensor and control and analysis means comprising at least two temperature dependent resistors including a reference resistor having a reference resistance and a measuring resistor coated with a catalytically active layer, said reference resistor and said measuring resistor being connected to each other to form a voltage divider;

means for exposing said measuring resistor to a medium to generate a reaction heat at said measuring resistor;

means for making said reference resistor inactive to said medium;

controlling means for keeping said reference resistance of said reference resistor constant, said controlling means including heating means for heating said at least two temperature dependent resistors, means for measuring a voltage drop across said reference resistor and means for processing said voltage drop across said measuring resistor to keep said reference resistance constant; and means for analyzing a change in a resistance value of said measuring resistor to determine the reaction heat when said measuring resistor is exposed to said medium.

2. Reaction heat sensor and control and analysis means as defined in claim 1, further comprising means for determining a change in a voltage drop across the measuring resistor as a result of said change in said resistance value of said measuring resistor.

3. Reaction heat sensor and control and analysis means as defined in claim 2, further comprising means for maintaining a current flowing through said measuring resistor constant.

4. Reaction heat sensor and control and analysis means as defined in claim 3, wherein said means for maintaining said current flowing through said measuring resistor constant comprises an alternating current generator, and further comprising voltage limiting means connected to said alternating current generator.

5. Reaction heat sensor and control and analysis means as defined in claim 1, wherein said heating means comprises a heating resistor and means for controlling a heating current flowing through said heating resistor.

6. Reaction heat sensor and control and analysis means as defined in claim 5, wherein said heating resistor is connected between a source of voltage and ground, said heating resistor being connected to ground via a switching means.

7. Reaction heat sensor and analysis means as defined in claim 6, wherein said switching means comprises a transistor and means for controlling said transistor depending on a voltage drop across said reference resistor.

8. Reaction heat sensor and control and analysis means as defined in claim 1, wherein said measuring resistor and said reference resistor are NTC-resistors.

9. Reaction heat sensor and control and analysis means as defined in claim 1, wherein said measuring resistor and said reference resistor are PTC-resistors.

10. Reaction heat sensor and control and analysis means as defined in claim 1, wherein said means for making said reference resistor inactive to said medium comprises a catalytically inactive layer applied to said reference resistor to render said reference resistor non-reactive to said medium.

11. Reaction heat sensor and control and analysis means as defined in claim 1, wherein said means for making said reference resistor inactive to said medium comprises a housing enclosing said reference resistor so as to separate said medium from said reference resistor.

* * * * *